United States Patent
Ehrismann

(10) Patent No.: US 8,117,003 B2
(45) Date of Patent: Feb. 14, 2012

(54) METHOD OF MONITORING AN ELECTROCHEMICAL HALF-CELL

(75) Inventor: Philippe Ehrismann, Uster (CH)

(73) Assignee: Mettler-Toledo AG, Greifensee (CH)

( * ) Notice: Subject to any disclaimer, the term of this patent is extended or adjusted under 35 U.S.C. 154(b) by 1104 days.

(21) Appl. No.: 11/950,975

(22) Filed: Dec. 5, 2007

(65) Prior Publication Data

US 2008/0149497 A1  Jun. 26, 2008

(30) Foreign Application Priority Data

Dec. 22, 2006 (EP) ..................................... 06127182

(51) Int. Cl.
 *G01N 27/26* (2006.01)
(52) U.S. Cl. ........................................ 702/116; 205/775
(58) Field of Classification Search .................. 205/775, 205/794, 794.5, 82; 702/116, 176
 See application file for complete search history.

(56) References Cited

U.S. PATENT DOCUMENTS

| | | | |
|---|---|---|---|
| 4,686,011 A | 8/1987 | Jackle | |
| 4,822,456 A | 4/1989 | Bryan | |
| 6,133,709 A * | 10/2000 | Puchianu | 320/116 |
| 6,685,807 B2 | 2/2004 | Meier | |
| 6,856,930 B2 | 2/2005 | Ammann | |
| 2005/0040038 A1 | 2/2005 | Berger et al. | |
| 2006/0070889 A1 | 4/2006 | Ehrismann | |

FOREIGN PATENT DOCUMENTS

| | | |
|---|---|---|
| DE | 19539763 A1 | 4/1997 |
| EP | 1219958 A1 | 7/2002 |

OTHER PUBLICATIONS

Diamond, D., ed., "2.2. Potentiometry" in Principles of Chemical and Biological Sensors, John Wiley & Sons, Inc., New York: 1998, pp. 20-21.*

* cited by examiner

*Primary Examiner* — J. Christopher Ball
(74) *Attorney, Agent, or Firm* — Standley Law Group LLP

(57) ABSTRACT

A method of monitoring an electrochemical second order half-cell (1, 101) is provided, as is a measuring probe with at least one electrochemical second order half-cell (101), a control- and/or regulation unit (7) to close an electrochemical contact between the half-cell and a measuring medium (8), and with at least one temperature sensor (9, 10). The half-cell includes an electrolyte (4) and a first conductor element (2) in contact with the electrolyte and which holds a first electrical potential ($E_1$). The half-cell also has a second conductor element (3) in contact with the electrolyte, the second conductor holding a second electrical potential ($E_2$). The two conductor elements (2, 3) comprise the same metal. The first conductor element has a coating (6) of a low-solubility salt of the same metal. The control- and/or regulation unit includes a program for executing a method of monitoring the electrochemical half-cell.

10 Claims, 3 Drawing Sheets

METHOD OF MONITORING AN ELECTROCHEMICAL HALF-CELL

CROSS-REFERENCE TO RELATED APPLICATIONS

This application claims a right of priority under 35 USC §119 from European patent application 06127182.1, filed 22 Dec. 2006, the content of which is incorporated by reference as if fully recited herein.

TECHNICAL FIELD

The invention relates to a method of monitoring an electrochemical second order half-cell as well as to a measuring probe with at least one electrochemical second order half-cell.

BACKGROUND OF THE ART

The known state of the art includes numerous kinds of electrochemical measuring systems or also measuring probes which have at least one electrochemical second order half-cell, for example ion-sensitive, potentiometric or redox measuring probes. These kinds of measuring probes are in everyday use for electrochemical measurements in analytical laboratories and process systems.

An electrochemical second order half-cell has a metallic conductor element arranged in an electrolyte which includes a saturated solution of a low-solubility salt of the metal of the conductor element. The conductor element is preferably coated with a surface layer of a low-solubility salt of the same metal of which the conductor element itself consists, wherein the salt contained in the surface coating and the salt dissolved in the electrolyte normally have the same anion. As is well known, the electrical potential of the conductor element, i.e. the electromotoric force E of this kind of a half-cell, is defined by the Nernst equation $$E = E^\circ - \frac{RT}{zF} \cdot \ln a, \quad [1]$$

wherein $E^\circ$ represents the standard electrode potential, R stands for the universal gas constant, T for the absolute temperature, z for the valence of the ion that determines the potential, or for the valance change in the case of a redox reaction, F stands for Faraday's constant, and a stands for the activity of the ion that determines the potential.

Half-cells of the known state of the art are based for example on the combinations silver/silver chloride (Ag/AgCl), calomel ($Hg/Hg_2Cl_2$), mercury sulfate ($Hg/HgSO_4$) or thalamide (Hg(Tl)/TlCl). While the redox combination of metal and metal ion is basically the determining factor for the potential, the respective metal ion activity in electrochemical second order half-cells is defined by the solubility product of the low-solubility metal salt and indirectly by the activity of its anion.

Measuring electrodes often consist of at least one reference half-cell and at least one measuring half-cell, with the latter also being referred to as glass half-cell, as for example in the case of a conventional pH electrode. The difference in the potentials occurring between two half-cells can be measured as a voltage. This measured voltage represents a measure for the ion activity or ion concentration. In particular for reference half-cells or for reference electrodes, several monitoring methods are already known.

A reference electrode for potentiometric measurements with a liquid electrolyte as well as a method of monitoring the fill level of the electrolyte by means of resistance measurements between several conductor elements, at least one of which is not immersed in the electrolyte, is disclosed in commonly-owned and co-pending US patent publication 2006/0070889 A1, by the present inventor.

In US patent publication 2005/0040038 A1 to Berger, a reference electrode with two separate chambers is disclosed wherein each chamber has a filling of electrolyte with a conductor element immersed in it. Since only one of the chambers is in contact with the measuring medium through a so-called liquid junction, for example a diaphragm, it is possible to detect changes taking place in the chamber that is in contact with the measuring medium by making a comparison measurement with the other chamber.

In U.S. Pat. No. 6,685,807, issued on 3 Feb. 2004 to Meier and commonly-owned by the assignee of this application, a method of monitoring the aging of a potentiometric measurement probe is disclosed, wherein a secondary conductor element is arranged at a shorter distance than a primary conductor element from the end of the measuring probe that is immersed in the measuring medium. An advancing electrolyte impoverishment first affects the measurement data of the secondary conductor element and is thus indicative of a progressing deficiency. Furthermore, a method for determining the remaining operating life of a potentiometric measuring probe is disclosed in published application DE 101 00 239 A1, where a secondary conductor element is arranged nearer to the end of the measuring probe that is immersed in the measuring medium than a primary conductor element. The remaining operating life is determined based on the difference between the respective potentials of the conductor elements as well as the basic operating time that has already elapsed.

The methods that are known from the prior art are oriented primarily towards monitoring the properties of the electrolyte and are based on the assumption that the conductor elements are always functioning in perfect order. However, this cannot simply be taken for granted, in particular for second order half-cells which are exposed to temperature fluctuations.

A known disadvantage of the electrochemical second order half cell lies in the considerable, non-uniform and partially discontinuous temperature dependency of the potential E of the conductor element. The reason for the not very transparent temperature dependency of these kinds of half-cells lies primarily in the generally strong temperature dependency of the solubility products of low-solubility compounds which causes the half-cell potential E to be temperature-dependent. The situation is further aggravated by the use of saturated saline solutions with the anion determining the potential, for example saturated solutions of potassium chloride or potassium sulfate in the electrolyte. The superposition of the two effects on each other leads to a highly undesirable discontinuous temperature behavior of the half-cell, as the solubilities of these salts likewise exhibit a pronounced temperature dependency. As an additional problem, the Nernst slope, i.e. the factor preceding the logarithmic term in equation [1], is likewise temperature-dependent. This is for example the reason why, if a reference electrode with a half-cell of this kind is used in setting up a measurement chain with a second measuring- or indicator half-cell, it is never possible to obtain an exactly defined point of intersection of isothermal curves as required for example for a temperature correction according to DIN 19265.

In addition to the temperature dependency that has just been described, measuring probes with second order half-cells suffer from two further severe drawbacks. It is possible in case of temperature changes that parts of the salt forming the surface coating get dissolved in the electrolyte and will be precipitated from the electrolyte when the temperature falls again. This manifests itself first of all in a pronounced hysteresis behavior, i.e. in a deviation of the electric potential when the temperature returns to the lower level that existed at the beginning.

In addition, given that in all of the aforementioned reference half elements the actual measuring ion activity is set by way of the solubility product of a low-solubility salt, and since in heterogeneous equilibriums of this kind between the solution and the solid substance there are certain kinetic retardants inherent which present themselves as over-saturation, the setting of the potential in these reference electrodes after a temperature change occurs only after a certain time delay. This leads to a sluggish response behavior in potentiometric measurements, which can be very harmful in industrial applications.

Frequent temperature changes can even lead to a complete decomposition or dissolution of the metal salt coating from the metallic conductor element, causing a deterioration of the response behavior of the half-cell and/or even an irreversible destruction of the half-cell.

In measuring probes that are installed in a process system, it would be desirable to have the capability to monitor the proper functioning of individual measuring probes and in particular the proper functioning of their half-cells, in order to be able to identify defective measuring probes quickly, simply and reliably and to replace them at the right time.

It is therefore the objective of the present invention to develop a method of monitoring an electrochemical second order half-cell, in particular to monitor the ability of the conductor element to function correctly, as well as to provide a measuring probe that is suitable to perform the method.

SUMMARY OF THE INVENTION

This objective is met by a method of monitoring an electrochemical second order half-cell. The half-cell cooperates with a control- and/or regulation unit to close an electrochemical contact between the half-cell and a measuring medium, and with at least one temperature sensor, and comprises an electrolyte and a first conductor element that is in contact with the electrolyte and holds a first electrical potential, more specifically a first half-cell potential. The half-cell further comprises a second conductor element which is likewise in contact with the electrolyte and holds a second electrical potential, more specifically a second half-cell potential. The two conductor elements consist essentially of a metal. The first conductor element further has a coating of a low-solubility salt of the same metal. This coating covers the conductor element at least in part. The method of monitoring an electrochemical cell encompasses several steps:

registering a temperature-time profile by means of the temperature sensor;

determining a first control value which is related to the temperature-time profile at one point in time;

comparing the first control value to a first limit value;

determining a second control value which establishes a mathematical connection between the first potential and the second potential at the point in time when the first limit value is attained and/or exceeded;

comparing the second control value to a second limit value; and generating a signal when the second control value has arrived at or fallen below the second limit value.

This method allows during operation of a half-cell to determine the point in time and/or the time window at which or during which temperature changes occur that are of a sufficient magnitude to detect a difference between the first and the second conductor element in the activities of the metal ion dissolved in the electrolyte. Strong and in particular rapidly occurring temperature changes can trigger a partial and/or total dissolution of the metal salt coating of the conductor element. By observing the potential-time profiles of the two conductor elements in relation to each other at this point in time or during this time window, it becomes possible to estimate the degree of coating remaining on the first conductor element and thus to estimate its ability to function properly.

If the second control value, which represents a measure for the difference between the respective potentials of the two conductor elements, reaches a given second limit value, this allows the conclusion that the first conductor element is insufficiently coated and that at least a partial dissolution of the metal salt coating has taken place. If both conductor elements have nearly the same potential, a total dissolution of the metal salt coating has taken place. The term "potential of the conductor element" in the present context is normally used synonymously with "half-cell potential".

When the second control value has arrived at or fallen below the second limit value, the control- and/or regulation unit generates a signal in the form of an acoustical, optical and/or electronic indication to alert the user to the partial or total loss of functionality of the half-cell. The signal can be delivered for example electronically by way of a measurement converter, also referred to as transmitter or, if applicable, through a coupler and a shared data bus, to a process computer and/or a lead computer for further processing.

Depending on the area of application of the half-cell, the temperature can be registered continuously or in regular and/or irregular time intervals as a temperature-time profile.

To calculate the first control value, the measured temperature values and the points in time when the measurements were made are entered into a mathematical relationship and a time- and temperature-dependent value and/or function is determined. Preferably, the first time derivative of the temperature or the temperature difference over a given time interval is used as control value, but further temperature- and time-dependent functions can of course also be used to determine the first control value. The first control value represents in particular rapid temperature changes of the kind that can occur in the half-cell for process-related reasons.

The determination of the second control value can encompass for example the measurement of a first voltage occurring between the first conductor element and a further half-cell due to a difference in their respective electrical potentials and the measurement of a second voltage occurring between the second conductor element and the further half-cell due to a difference in their respective electrical potentials. The second control value or a second control function is determined dependent on the two voltages, for example as a voltage difference.

As an alternative, the determination of the second control value can encompass the measurement of a further voltage which occurs between the first and the second conductor element and which is measurable as long as the first conductor element is sufficiently coated and a difference exists between the respective potentials of the conductor elements. This step is advantageous, because the first and the second potential are thereby brought into a direct connection to each other without being influenced by the pH value or another property of the measuring medium.

If a continuous temperature-time profile is measured, it suggests itself to determine a temperature- and time-dependent first control function instead of individual first control values.

Like the temperature-time profile, the first potential and/or the second potential can be measured continuously or in regular and/or irregular time intervals as a potential-time profile.

The method of monitoring the half-cell, in particular the steps c to f, can be repeated in given time intervals or continuously.

The first control value can be determined as a discrete value of a time-dependent control profile or of a control function at one or more given points in time. Preferably, the first control value should be determined in regular time intervals, in particular before the start of a process or reaction.

It suggests itself to incorporate a method of this kind as a program in a control- and/or regulation unit of a measuring probe for the monitoring of an electrochemical second order half-cell. Besides the control- and/or regulation unit for closing an electrochemical contact between the half-cell and a measuring medium, the half-cell comprises at least one temperature sensor and at least one electrochemical second order half-cell. The half-cell comprises an electrolyte and a first conductor element that is in contact with the electrolyte and holds a first electrical potential. The half-cell further comprises a second conductor element which is in contact with the electrolyte and holds a second potential. The two conductor elements contain essentially the same metal. The first conductor element further comprises a coating of a low-solubility salt of the same metal. This coating covers the first conductor element at least partially.

The metal in the conductor elements can for example be silver, mercury, thallium, lead, or an alloy of these metals. The first conductor element is coated with a low-solubility metal salt of the same metal and/or of the same metal alloy, wherein the salt is preferably a metal chalcogenide, metal halogenide or metal sulfate, and in particular a metal chloride, -sulfide, -bromide or -sulfate. The attribute "low-solubility" relates primarily to the solubility of the metal salt in the solvent used for the electrolyte.

The range of electrolytes that can be used includes liquid as well as solidified electrolytes. Known electrolytes include for example soluble metal salts that have the same anion as the coating, such as potassium chloride, sodium chloride, magnesium chloride, sodium sulfate or potassium sulfate. Also known are polymer electrolytes on acrylamide-acrylate basis. In principle, all electrolytes can be used that are known as suitable for electrochemical second order half-cells.

Measurement probes of this kind can be configured for example as ion-sensitive, potentiometric or redox measuring probes and in particular as pH measuring probes.

The method as described can be executed in principle with all measuring probes that include a second order half-cell and where a stable potential under rapid temperature changes is important.

BRIEF DESCRIPTION OF THE DRAWINGS

The method and devices of the present invention will be better understood when reference is made to the accompanying drawings, wherein identical parts are identified by identical reference numbers and wherein.

DETAILED DESCRIPTION OF THE DISCLOSED EMBODIMENTS

Figure 1:
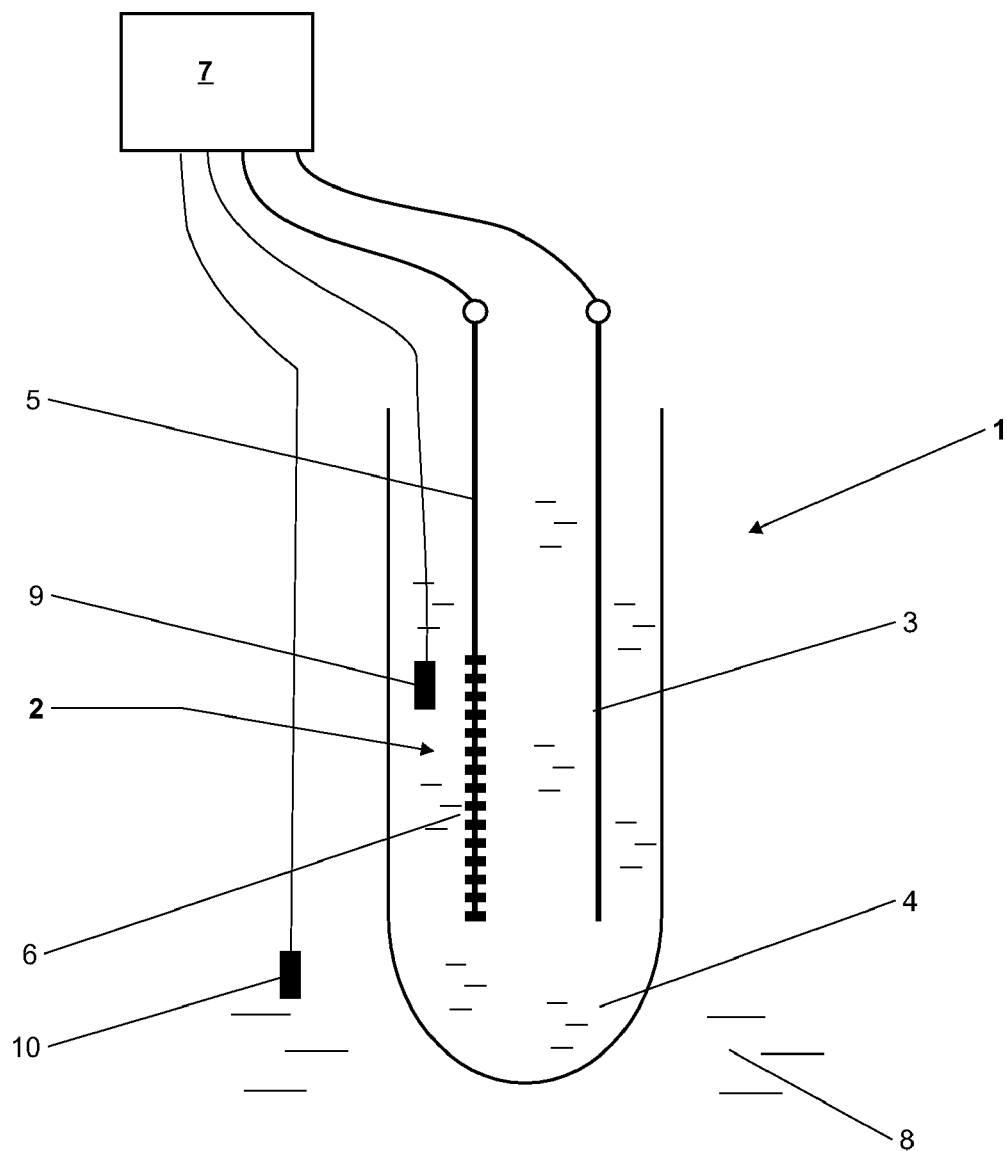
FIG. 1 schematically illustrates an electrochemical second order half-cell with a first and a second conductor.

An electrochemical second order half-cell 1 with a first conductor element 2 and a second conductor element 3 is represented schematically in FIG. 1. Both of the conductor elements 2 and 3 are immersed in an electrolyte 4. The first conductor element 2 consists of a metal wire 5 which is at least partially covered with a coating 6 of a low-solubility metal salt. The second conductor element 3 consists of the same metal and is not coated. For the combination of a metal with a metal salt, one can use for example Ag/AgCl, $Hg/Hg_2Cl_2$, Hg(Tl)/TlCl or other systems known in the state of the art for electrochemical half-cells.

The conductor elements 2, 3 are connected to a control-and/or regulation unit 7 as symbolically indicated here, which is designed to close the electrochemical circuit between the half-cell 1 and the measuring medium 8 with which the half-cell 1 is in contact.

The control- and/or regulation unit 7 in this example is configured as a computer or microcomputer. In case the half-cell 1 is part of a measuring probe, the control- and/or regulation unit 7 can either be directly incorporated in the measuring probe, for example as a transmitter, or it can be configured as an external unit.

Furthermore, the control- and/or regulation unit 7 serves to register the temperature of the half-cell 1. This temperature can be measured either with a temperature sensor 9 that is arranged directly in the half-cell and/or with a temperature sensor 10 that is arranged in the measuring medium 8.

Figure 2:
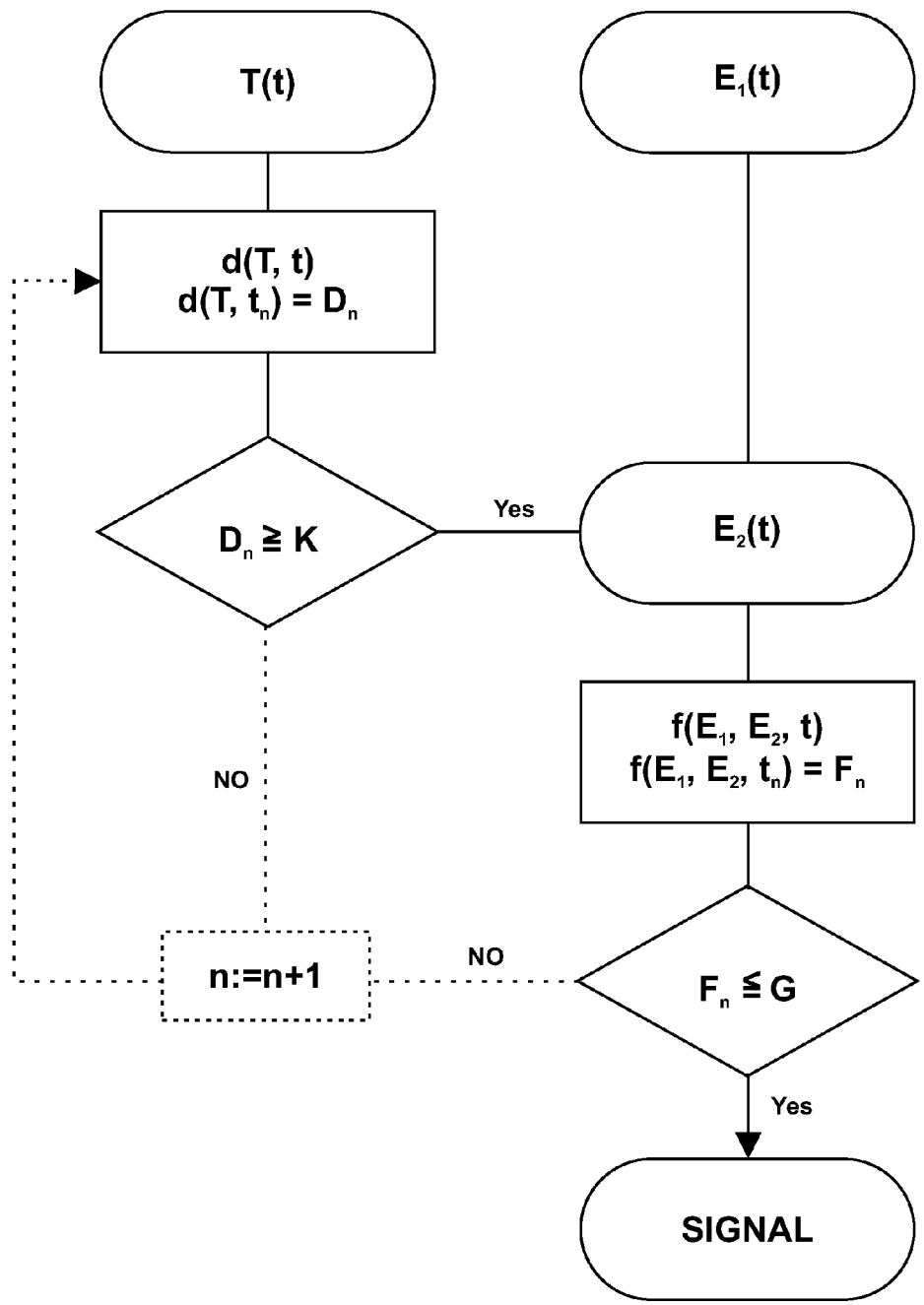
FIG. 2 is a flowchart of a method for checking the proper functioning of an electrochemical second order half-cell.

FIG. 2 schematically illustrates a method of monitoring a second order half-cell as shown in FIG. 1. This method is preferably incorporated directly in the control- and/or regulation unit as a program and/or as part of an operating program of the half-cell. It is further possible that the measurement data of the half-cell are sent on to a central unit and that the monitoring method is implemented in the central unit.

The data that are being measured are the temperature $T(t)$ of the electrolyte in the half-cell and/or in the measuring medium as well as the potential $E_1(t)$ of the first conductor element as a function of time. Preferably, these data are determined continuously, but a discrete determination of measurement data is also possible.

Based on the temperature-time profile $T(t)$ that has been found, the next step is to determine a first control function $d(T,t)$ which depends at least on the temperature and the time and consists in the simplest case of the derivative $dT/dt$ of the temperature with respect to time. The first control function $d(T,t)$ can of course be any other mathematical function that is dependent on the time and the temperature. The choice of the function depends primarily on the area of application of the half-cell or on the nature of the measuring probe that contains a half-cell.

Either at predetermined points in time $t_n$ or continuously, a first control value $D_n = d(T,t_n)$ is calculated by means of the first control function $d(T,t)$. This first control value $D_n$ is then compared to a first limit value K.

The first limit value K represents a measure for the temperature changes to which the half-cell is exposed during the time interval and which are a critical factor for the advancement of the dissolution process and the decomposition of the metal salt coating on the first conductor element.

As long as the first control value $D_n$ is smaller than the first limit value K, the counter n for the time interval $t_n$ is incremented only by one, and a new first control value $D_{n+1}$ is determined at the next point in time $t_{n+1}$.

When the first control value $D_n$ has reached or passed beyond the first limit value K, i.e. if $D_n \geq K$, a second control value $F_n$ and/or a second control function $f(E_1, E_2, t)$ is determined, whereby a correlation is established between the first potential $E_1$ of the first conductor element and the second potential $E_2$ of the second conductor element at the same point in time $t_n$.

At the time $t_n$ when the first control value $D_n$ is larger than or equal to the first control value $D_n \geq K$, a second control value $F_n = f(E_1, E_2, t_n)$ is determined by means of the second control function $f(E_1, E_2, t)$ and compared to a second limit value G.

The second control value $F_n$ represents a measure for the extent to which the degradation or dissolution of the coating of the first conductor element has progressed.

The relationship $f(E_1, E_2, t)$ between the respective potentials $E_1$, $E_2$ of the first and the second conductor element and the time can be determined directly by registering a voltage $U_{1,2}(t)$ occurring between the two conductor elements as a function of time. The voltage $U_{1,2}(t)$ is a direct measure for the difference between the respective potentials of the two conductor elements and is used directly as control value $F_n = f(E_1, E_2, t_n) = U_{1,2}(t_n)$.

Furthermore, the respective voltages $U_1$ and $U_2$ which occur between the first conductor element and a further half-cell as well as between the second conductor element and the further half-cell can be determined as functions of time $U_1(t)$, $U_2(t)$. The voltages $U_1(t)$, $U_2(t)$ depend on the respective potentials $E_1$, $E_2$ of the first and the second conductor element. The control value $F_n$ and/or the control function $f(E_1, E_2, t)$ which depend on the two potentials $E_1$, $E_2$ as well as on the time can be determined for example by forming the difference between the measured voltages $U_1$, $U_2$. The control value $F_n = f(E_1, E_2, t_n)$ represents the value of the control function $f(E_1, E_2, t)$ at a specific time $t_n$.

As long as the second control value $F_n$ is larger than the limit value G, it can be assumed that the first conductor element is sufficiently coated.

However, when the second control value $F_n$ reaches or even passes below the limit value G, the coating of the first conductor element is no longer sufficient, as too much of the metal salt of the coating has passed into the solution and/or has been precipitated. The control- and/or regulation unit will in this case generate a signal which indicates to the user that the half-cell or a measuring probe that includes the half-cell has lost part or all of its ability to function and should be replaced shortly.

Figure 3:
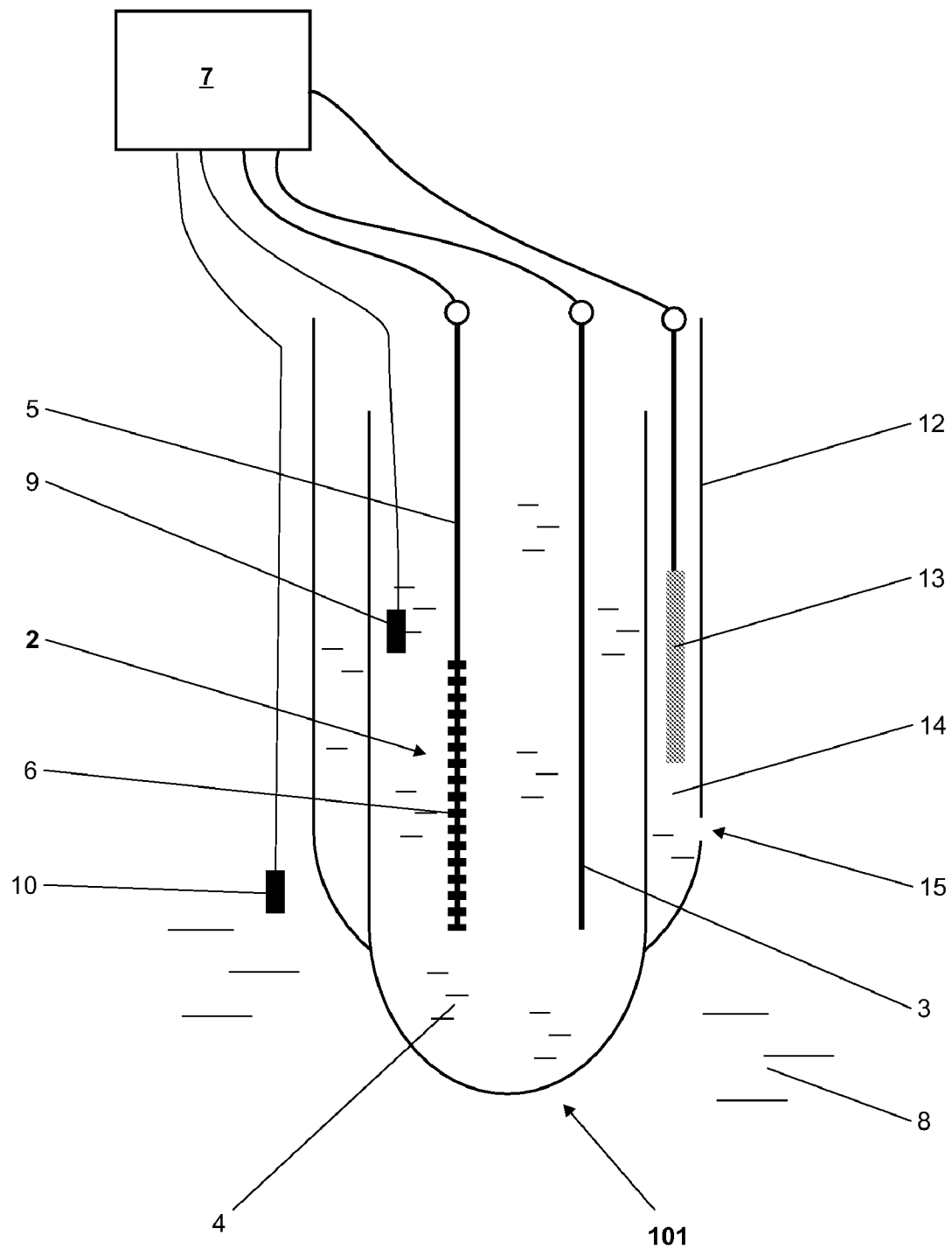
FIG. 3 schematically represents a pH measuring probe with an electrochemical second order half-cell with a first and a second conductor element and a reference half-cell.

A half-cell according to the invention can for example be used as a measuring half-cell 101 in a pH measuring probe of the kind that is represented schematically in FIG. 3. Elements that are analogous to those shown in FIG. 1 are identified by the same reference numerals.

The measuring half-cell 101 is surrounded by a reference half-cell 12 which is in contact with a measuring medium 8 by way of a so-called liquid junction 15. Arranged in the reference half-cell is a third metallic conductor element 13. The third conductor element 13 can be any conductor element that is suitable for pH measurements. The reference half-cell 12 is filled with a second electrolyte 14. Regarding the function of electrochemical pH measuring probes the reader is referred to the known state of the art as described in the technical literature.

What is claimed is:

1. A method of monitoring the operation of a probe in a measuring medium, the method comprising the steps of:
providing a probe, comprising:
an electrochemical second order half-cell, the half-cell comprising:
an electrolyte;
a first and a second conductor element, comprising the same metal, each of the conductor elements in contact with the electrolyte, such that the first conductor element holds a first electrical potential and the second conductor element holds a second electrical potential as a result of the contact, the first conductor element coated with a low-solubility salt of the metal comprising the conductor elements;
a control- and/or regulation unit for closing an electrochemical contact between the half-cell and the measuring medium, the control and/or regulation unit comprising a program for monitoring the electrochemical half-cell; and
a temperature sensor;
registering a temperature-time profile in the control- and/or regulation unit, using the temperature sensor;
determining, in the program of the control- and/or regulation unit, a first control value, related to the registered temperature-time profile for at least one point in time;
comparing, in the program of the control- and/or regulation unit, the determined first control value to a first limit value;
determining, in the program of the control- and/or regulation unit, a second control value that establishes a mathematical connection between the first electrical potential and the second electrical potential for at least one point in time when the first control value is equal to or greater than the first limit value;
comparing, in the program of the control- and/or regulation unit, the determined second control value to a second limit value; and
generating a signal from the control- and/or regulation unit when the determined second control value is equal to or less than the second limit value.

2. The method of claim 1, wherein:
the step of determining the second control value comprises the substeps of:
providing a further electrochemical half-cell;
measuring a first voltage occurring between the first conductor element and the further half-cell; and
measuring a second voltage occurring between the second conductor element and the further half-cell.

3. The method of claim 1, wherein:
the step of determining the second control value comprises the substep of:
measuring a further voltage occurring between the respective first and second conductor elements.

4. The method of claim 1, wherein:
the step of registering the temperature-time profile is achieved by determining the temperature continuously or in regular or irregular time intervals.

5. The method of claim 1, wherein:
the step of determining the first control value entails the mathematical derivative of the temperature with respect to time.

6. The method of claim 2, wherein:
the steps of measuring voltages is achieved by determining the voltage either continuously or in regular or irregular time intervals as a voltage-time profile.

7. The method of claim 1, wherein:
the steps of:
- determining the first control value;
- comparing the determined first control value to a first limit value;
- determining the second control value;
- comparing the determined second control value to a second limit value; and
- generating a signal;

are repeated in given time intervals or continuously.

8. The method of claim 1, wherein:
the step of determining the first control value is achieved by determining a discrete value of a control profile for at least one given point in time.

9. The method of claim 3, wherein:
the steps of measuring voltages is achieved by determining the voltage either continuously or in regular or irregular time intervals as a voltage-time profile.

10. The method of claim 2, wherein:
the step of registering the temperature-time profile is achieved by determining the temperature continuously or in regular or irregular time intervals.

* * * * *